United States Patent
Bombardelli

[11] Patent Number: 5,973,204
[45] Date of Patent: Oct. 26, 1999

[54] COLCHICINE AND THIOCOLCHICINE DERIVATIVES WITH ANTIINFLAMMATORY AND MUSCLE RELAXANT ACTIVITIES

[75] Inventor: Ezio Bombardelli, Milan, Italy

[73] Assignee: Indena S.p.A., Milan, Italy

[21] Appl. No.: 09/056,365

[22] Filed: Apr. 7, 1998

[30] Foreign Application Priority Data

Apr. 11, 1997 [IT] Italy .................... MI97A0845

[51] Int. Cl.⁶ .................... C07C 233/00; A01N 37/18
[52] U.S. Cl. .................... 564/222; 514/630
[58] Field of Search .................... 514/630; 564/222

[56] References Cited

U.S. PATENT DOCUMENTS 2,820,029  1/1958  Muller et al. .................... 260/210

FOREIGN PATENT DOCUMENTS 0 356 137   2/1990   European Pat. Off. .
1 344 474   2/1964   France .
WO 97 01570 1/1997   WIPO .

OTHER PUBLICATIONS

Grant & Hackh's Chemical Dictionary, 5th Edition, col. 1, p. 113, Feb. 24, 1988.
Kerekes et al., "Synthesis and Biological Effects of Novel Thiocochicines"; J. Med. Chem., vol. 28, No. 9, 1985, pp. 1204–1208, XP002069840.

Primary Examiner—Dwayne C. Jones
Attorney, Agent, or Firm—Pennie & Edmonds LLP

[57] ABSTRACT

The present invention relates to 3-demethyl-thiocolchicine derivatives of general formula (I)

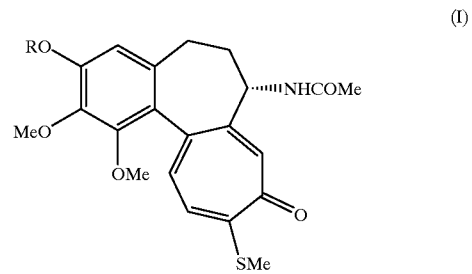

in which R can be

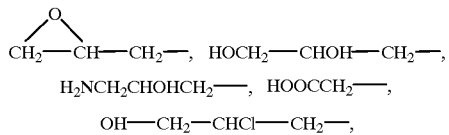

to a process for the preparation thereof, to pharmaceutical compositions containing them and to the use thereof for the preparation of medicaments with muscle relaxant and anti-inflammatory activities.

1 Claim, No Drawings

COLCHICINE AND THIOCOLCHICINE DERIVATIVES WITH ANTIINFLAMMATORY AND MUSCLE RELAXANT ACTIVITIES

TECHNICAL FIELD

The present invention relates to 3-demethyl-thiocolchicine derivatives of general formula (I):

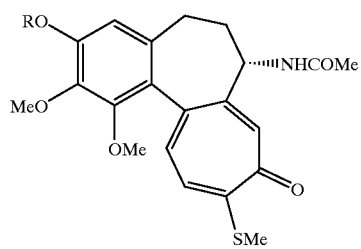

in which R is selected from

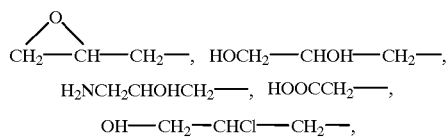

which will be hereinafter referred to as compounds I, II, III, IV and V respectively), to a process for the preparation thereof, to pharmaceutical compositions containing them and to the use thereof in the rheumathologic-orthopedic field, for the preparation of medicaments with muscle relaxant and antiinflammatory activities.

BACKGROUND OF THE INVENTION

Muscle relaxant medicaments have the common characteristic of reducing the muscle tone, for example in muscle contractures.

Muscle contracture is a feature characterizing a number of pathologies of the locomotor apparatus, and it is one of the major factors responsible for the persistence of the painful condition related thereto. Muscle contracture also occurs in the inflammatory-rheumathic and degenerative orthopedic pathologies; when affecting an articulation, it causes, in addition to pain, a stiffening which limits the mutual mobility of the joint extremities and therefore the functionality of the part involved. Due to these reasons, there is a great interest in molecules characterized by remarkable muscle relaxant and antispastic properties.

Colchicine is known to be a pseudo-alkaloid used widely and for a very long time in therapy for the treatment of gout. Likewise widely used in therapy is of 3-demethyl-thiocolchicine glucoside, namely thiocolchicoside, as an antispastic in the inflammatory processes against skeletal muscles (Ortopedia e Traumatologia Oggi XII, n. 4, 1992). Recently, thiocolchicoside activity has been proved to be related to its interaction with strychnine-sensitive glycine receptors, therefore compounds having glycine-mimetic activity can be used in the rheumathologic-orthopedic field thanks to their muscle relaxant characteristics.

SUMMARY OF THE INVENTION

The invention relates, in a first embodiment, to an anti-inflammatory and muscle-relaxant composition comprising a therapeutic amount of at least one 3-demethyl-thiocolchicine derivative having the formula

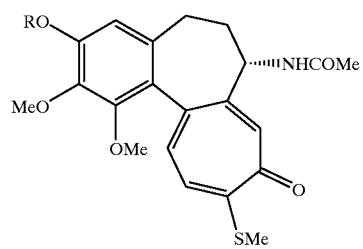

wherein R can be

CH$_2$—CH—CH$_2$— (with epoxide O)

HOCH$_2$—CHOH—CH$_2$—, H$_2$NCH$_2$CHOHCH$_2$—, HOOCCH$_2$— or HO—CH$_2$—CHCl—CH$_2$—.

In another embodiment the invention relates to a method of preparing an anti-inflammatory and muscle-relaxant composition comprising, as an active ingredient, a therapeutic amount of at least one 3-demethyl-thiocolchicine derivative having the formula

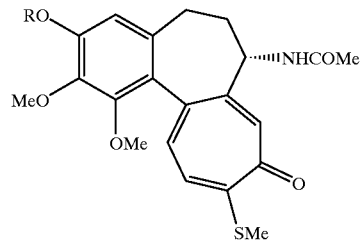

wherein R can be

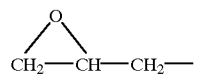

HOCH$_2$—CHOH—CH$_2$—, H$_2$NCH$_2$CHOHCH$_2$—, HOOCCH$_2$— or HO—CH$_2$—CHCl—CH$_2$—.

wherein the method comprises forming the active ingredient by use of the following reaction scheme:

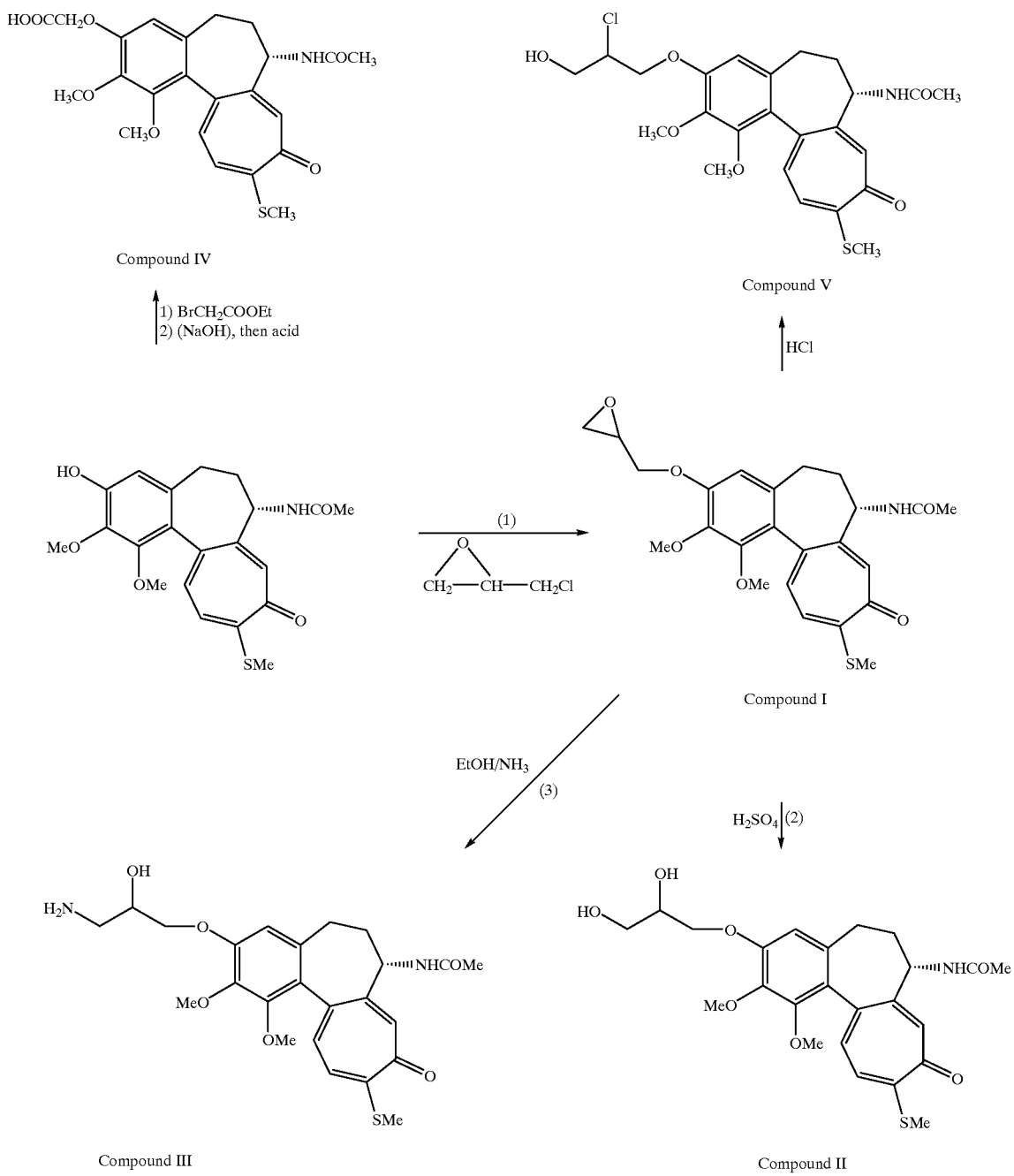

and admixing the active ingredient with one or more pharmaceutically acceptable carriers and/or excipients. The subject composition(s) may be prepared in the form of capsules, tablets, granulates, suppositories, creams, injectable solutions, ointments and/or gels.

A further embodiment of the invention involves the treatment of muscular inflammation in a human patient by administering to said patient a therapeutically effective dosage of the one or more compositions described above. Still further, these compositions may also be administered to patients in therapeutic dosages for the purpose of inducing muscle relaxation in such patients. The compositions may be administered in a variety of manners well known in the art, including by intramuscular injection, wherein the preferred dosage is less than 5 mg/kg of the patient's body weight and more preferably, about 1 mg/kg.

DETAILED DESCRIPTION OF THE INVENTION

It has now been discovered that thiocolchicine derivatives of general formula (I) are capable of exerting an effective muscle relaxant action, evaluated by studies both in vitro and in vivo, at remarkably more advantageous doses than those commonly used for similar known substances.

The compounds of the invention have shown in binding tests a higher affinity to glycine receptors (Table I) than a structurally similar compound, i.e. thiocolchicoside.

TABLE I

| Compound | µM concentration | % displacement |
|---|---|---|
| thiocolchicoside | 0.1 | 20 |
|  | 0.5 | 45 |
|  | 1 | 70 |
| Compound I | 0.1 | 40 |
|  | 1 | 85 |
| Compound II | 0.1 | 35 |
|  | 1 | 65 |
| Compound III | 0.1 | 50 |
|  | 1 | 75 |

The interaction of the compositions of the invention with their receptors has been evaluated according to the procedure by A. B. Young and S. H. Snyder reported in Proc. Natl. Acad. Sci U.S.A. 71, 4002, 1974.

The inhibition of the polysynaptic reflexes induced by strychnine in rabbits has been studied for the in vivo tests.

Using this model, the compounds of the invention, injected at doses of 1 mg/kg intramuscularly, were capable of reducing polysynaptic reflexes by 50% (compound I), by 60% (compound II) and by 65% (compound III), and of removing completely the potentiation of strychnine-induced reflexes at the same doses; the control molecule thiocolchicoside was administered at minimum doses of 5 mg/kg to obtain comparable effects.

Moreover, the compounds of formula (I) have an acute toxicity significantly lower than thiocolchicoside. The $DL_{50}$ of the compounds I–III is, in fact, higher than 30 mg/kg i.v. in the mouse, the $DL_{50}$ of thiocolchicoside being 7.5 mg/kg.

In vitro cytotoxicity tests on cells of breast carcinoma and of other tumors proved that the compounds of the invention are not cytotoxic up to concentrations higher than 5000 nM, whereas parent thiocolchicine is cytotoxic even at a concentration of 0.6 nM.

In conclusion, the compounds of the invention are safe and therapeutically advantageous.

The compounds I–V can be prepared starting from 3-demethylthiocolchicine, according to the following general reaction scheme, using conventional reagents and synthetic procedures.

Scheme 1

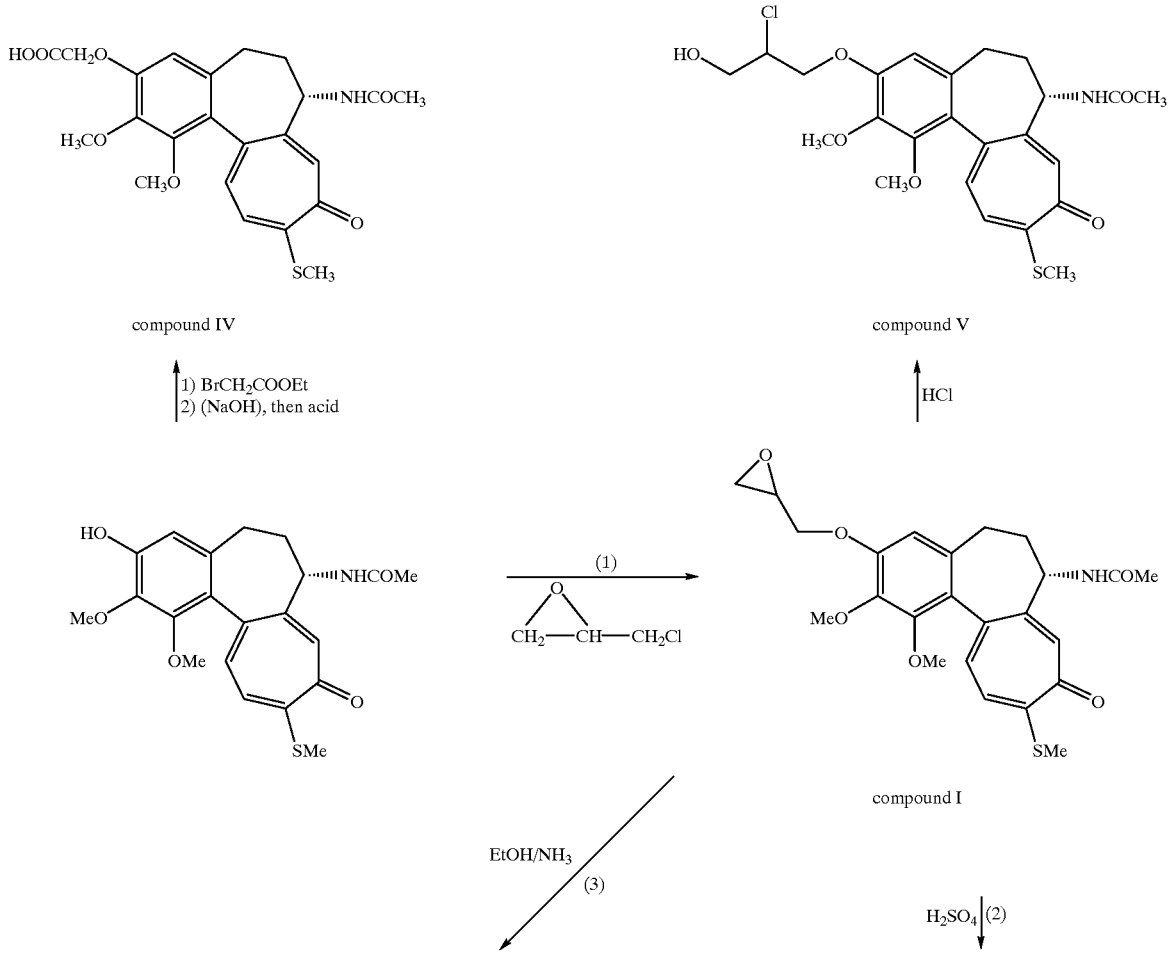

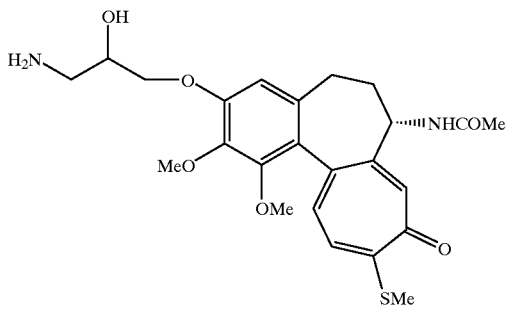

compound III

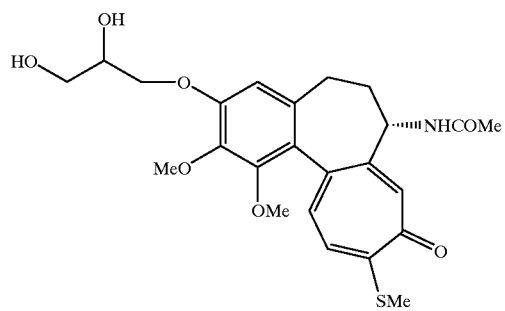

compound II

For the use in therapy, compounds I–V can be suitably formulated using pharmaceutically acceptable excipients and carriers, in forms such as capsules, tablets, granulates, suppositories, creams, injectable solutions, ointments, gels and others, more generally according to conventional techniques, such as those described in "Remington's Pharmaceutical Sciences Handbook", Mack Publishing Company, New York, U.S.A., 17th Ed., 1985.

Therefore, the present invention further relates to pharmaceutical compositions containing a compound of general formula I for use as muscle relaxants, antispastics, antiinflammatories, antigouts, more generally in the rheumathologic-orthopedic field.

The following examples further illustrate the invention.

EXAMPLE I

Synthesis of 3-demethyl-3-glycidylthiocolchicine

3-Demethylthiocolchicine (200 mg, 0.5 mmol) is suspended in $CH_3CN$ (10 ml). The mixture is refluxed, then added with 1,8-diazobicyclo[5.4.0]undec-7-ene (DBU, 153 μl, 1 mmol). The product solubilizes immediately, and the solution darkens. After the addition, (±)-epichlorohydrin (3 mmol, 190 μl) is added. The reaction is monitored via TLC ($CCH_2Cl_2$—MeOH 9-1). After 7 hours, the starting product has reacted completely. The solvent is evaporated off and the reaction crude is purified by gravimetric chromatography on silica gel, eluting with a $CH_2Cl_2$—MeOH 100-2 mixture. The resulting oily product (160 mg, 0.35 mmol, yield: 70%) is crystallized from acetone and identified on the basis of the $^1H$-$^{13}C$-NMR, COSY and NOESY spectra.

The formed product is a mixture of the two diastereomers (2'R, 7S, aS) and (2'S, 7S, aS).

m.p.: 241–241.5° C.

$^1H$-NMR: ($CDCl_3$) 7.84–7.79 (m, 1H), 7.42 (s, 1H), 7.31 (d, 1H, J 10.3), 7.08 (d, 1H, J 10.3), 6.57, 6.56 (2s, 1H), 4.66–4.61 (m, 1H), 4.37–4.28 (m, 1H), 4.10–3.98 (m, 1H), 3.94 (s, 3H), 3.65 (s, 3H), 3.44–3.37 (m, 1H), 2.96–2.91 (m, 1H), 2.82–2.76 (m, 1H), 2.43 (s, 3H), 2.48–1.85 (m, 4H), 1.97 (s, 3H).

$^{13}C$-NMR: ($CDCl_3$) 162.5, 170.2, 158.4, 152.7, 152.0, 151.4, 142.3, 138.6, 135.0, 134.5, 128.4, 126.8, 126.7, 109.6, 109.5, 70.4, 70.1, 61.7, 61.5, 52.4, 50.3, 44.7, 36.4, 29.9, 22.9, 15.2.

EXAMPLE II

Synthesis of 3-demethyl-3-(2,3-dihydroxyrpropyl) thiocolchicine

3-Demethyl-3-glycidylthiocolchicine (300 mg, 0.67 mmol) is dissolved in a dioxane-$H_2O$ (1–1.5 ml) mixture and treated with a catalytic amount of 0.2 N $H_2SO_4$, then heated to reflux. The reaction is monitored by TLC ($CH_2CL_2$—MeOH 9-1). After 5 hours, the solvent is evaporated off and the reaction crude is purified by gravimetric chromatography on silica gel, eluting with a $CH_2Cl_2$—MeOH 100-3 mixture. The desired product (identified on the basis of its spectroscopic properties: $^1H$-$^{13}C$-NMR and COSY) is obtained in a 73% yield (228 mg, 0.48 mmol) as a mixture of the two diastereomers (2'R, 7S, aS) and (2'S, 7S, aS).

m.p.: 149–150° C., dec.

$^1H$-NMR ($CDCl_3$) 7.28 (d, 1H, J 9.8), 7.26 (s, 1H), 7.06 (d, 1H, J 9.8), 6.58 (s, 1H), 6.48 (d, 1H, J 8.5), 4.71–4.60 (m, 1H), 4.20–4.11 (m, 4H), 3.94 (s, 3H), 3.85–3.82 (m, 1H), 3.65 (s, 3H), 2.60–1.92 (m, 4H), 2.44 (s, 3H), 1.99 (s, 3H).

$^{13}C$-NMR ($CDCl_3$) 182.5, 170.0, 158.5, 152.6, 151.5, 142.2, 138.2, 134.8, 134.7, 128.4, 126.8, 126.7, 109.6, 92.5, 71.7, 70.2, 63.8, 61.7, 52.3, 36.6, 29.9, 23.0, 15.3.

EXAMPLE III

Synthesis of 3-demethyl-3-(3-amino-2-hydroxypropyl)thiocolchicine

3-Demethyl-3-glycidylthiocolchicine (300 mg, 0.67 mmol) is dissolved in ammonia-saturated EtOH and heated to 60° C. After 1 hour the reaction is completed, and the reaction solvent is evaporated off to give the desired product in a pure state, in an 83% yield (261 mg, 0.55 mmol), as a mixture of the two diastereomers (2'R, 7S, aS) and (2'S, 7S, aS). The product is identified on the basis of the its spectroscopical properties: $^1H$-NMR.

m.p.: 144.8–145.5° C., dec.

$^1H$-NMR: ($CDCl_3$) 7.28 (d, 1H, J 10.6), 7.26 (s, 1H), 7.06 (d, 1H, J 10.6), 4.72–4.58 (m, 1H), 4.12–3.90 (m, 4H), 3.94 (s, 3H), 3.65 (s, 3H), 3.05–1.5 (m, 5H), 2.44 (s, 3H), 1.99 (s, 3H).

EXAMPLE IV

Synthesis of 2-(3-demethylthiocolchicine)acetic acid

3-Demethylthiocolchicine (401 mg, 1 mmol) is suspended in dry $CH_3CN$ (10 ml) at room temperature. 1,8-Diazabicyclo[5.4.0]undec-7-ene (DBU) (192 ml, 1.3 mmol) is added dropwise: the mixture solubilizes and darkens. After the addition, ethyl bromoacetate (161 ml, 1.3 mmol) is added, the solution thereby slowly lightening. After about 2 hours, a further 60 ml of DBU and 70 ml of the ester are added. The reaction mixture is left at room temperature for 10 hours. TLC: $CH_2Cl_2$—MeOH=9/1.

The solvent is evaporated off under reduced pressure and the resulting crude is purified by gravimetric chromatography with a polarity gradient, eluting with the $CH_2Cl_2$—MeOH mixture. The desired ester (410 mg) is obtained in an 84% yield. The product is identified on the basis of its spectroscopic properties.

m.p.: 115° C.

$^1$H NMR (CDCl$_3$): 1.31 (t, J7.1, 3H, Me), 1.97 (s, 3H, MeCO), 1.8–2.5 (m, 4H, H-5, H-6), 2.43 (s, 3H, SMe), 3.66, 3.98 (two s, 6H, OMe), 4.25 (q, J7.1, 2H, OCH$_2$Me), 4.58–4.70 (m, 1H, H-7), 4.72 (s, 2H, OCH$_2$), 6.46 (s, 1H, H-4), 7.08 (d, J10.6, 1H, H-11), 7.29 (d, J10.6, 1H, H-12), 7.27 (s, 1H, H-8), 7.85 (d, J6.9, 1H, NH).

NaOH pellets (32 mg, 0.8 mmol) are dissolved in 5% aqueous EtOH (10 ml). 2-(3-Demethylthiocolchicine)ethyl acetate (300 mg, 0.62 mmol) is added, and the reaction is left at room temperature under magnetic stirring. After 1 hour, (TLC: $CH_2Cl_2$—MeOH=9/1), the solvent is evaporated off and the residue is dissolved in a HCl diluted aqueous solution. A yellow product precipitates, which is further purified by chromatography on silica gel, eluting with the $CH_2Cl_2$—MeOH 9-1 mixture. 2-(3-Demethylthiocolchicine)acetic acid (260 mg) is obtained in a 92% yield.

m.p.: 189–190 dec.°C. (acetone)

$^1$H NMR (CDCl$_3$): 1.95 (s, 3H, MeCO), 1.75–2.58 (m, 4H, H-5, H-6), 2.44 (s, 3H, SMe), 3.03 (s, 1H, COOH) 3.64, 3.97 (two s, 6H, OMe), 4.51–4.70 (m, 1H, H-7), 4.73 (s, 2H, OCH$_2$), 6.61 (s, 1H, H-4), 7.12 (d, J10.7, 1H, H-11), 7.31 (d, J10.7, 1H, H-12 and NH), 7.50 (s, 1H, H-8).

3-Demethyl-3-(2-chloro-3-hydroxypropyl)thiocolchicine has been obtained following a similar procedure to that of the examples above.

m.p.: 118–119 dec. (acetone i-Pr$_2$O)

$^1$H NMR (CDCl$_3$): 1.99 (s, 3H, MeCO), 1.75–2.58 (m, 4H, H-5, H-6), 2.44 (s, 3H, SMe), 3.07 (t, 1H, OH, deuterable), 3.66, 3.94 (two s, 6H, OMe), 3.77–3.87, 4.15–4.32 (two m, 2+3H, CH$_2$CHCH$_2$), 4.57–4.70 (m, 1H, H-7), 6.58 (s, 1H, H-4), 7.14 (d, J10.6, 1H, H-11), 7.29 (d, J10.6, 1H, H-12), 7.35 (m, 1H, NH), 7.37 (s, 1H, H-8).

EXAMPLE V

Example of formulation of the compounds of formula (I) in the form of vials.

| Vials | |
|---|---|
| Compound II | 5 mg |
| Sodium chloride | 15.8 mg |
| Water for injectable preparations q.s. to | 2 ml |

EXAMPLE VI

Example of formulation of the compounds of formula (I) in the form of capsules.

| Hard gelatin capsules | |
|---|---|
| Compound II | 10 mg |
| Lactose | 212.3 mg |
| Starch | 1.3 mg |
| Magnesium stearate | 2.4 mg |

EXAMPLE VII

Example of formulation of the compounds of formula (I) in the form of cream.

| Cream | |
|---|---|
| Compound II | 0.5 g |
| Methyl p-hydroxybenzoate | 0.14 g |
| Ethyl p-hydroxybenzoate | 0.035 g |
| Polyoxyethylene-20-sorbitan monooleate | 5 g |
| Sodium lauryl sulfate | 2 g |
| Spermaceti | 5 g |
| Cetyl alcohol | 7 g |
| Hydrogenated lanolin | 12.5 g |
| Stearic acid | 8 g |
| Sodium alginate | 0.5 g |
| Lavender oil | 1 g |
| Depurated water q.s. to | 100 g. |

I claim:

1. An anti-inflammatory and muscle relaxant composition comprising a therapeutic amount of at least one 3-demethyl-thiocolchicine derivative having the formula

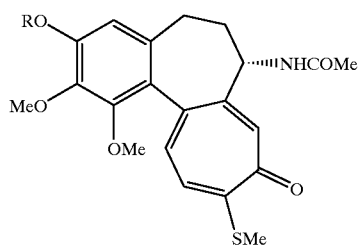

(I)

wherein R is selected from the group consisting of

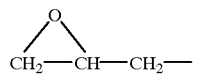

$HOCH_2$—$CHOH$—$CH_2$—, $H_2NCH_2CHOHCH_2$—, $HOOCCH_2$— and HO—$CH_2$—$CHCl$—$CH_2$—.

* * * * *